United States Patent [19]

Donnerback et al.

[11] Patent Number: 4,784,140

[45] Date of Patent: Nov. 15, 1988

[54] DEVICE FOR CARRYING OUT CRYOTHERAPY

[75] Inventors: Andreas Donnerback, Krefeld; Klemens Thoma, Krefeld-Huls; Wolfgang Volker, Tonisvorst, all of Fed. Rep. of Germany

[73] Assignee: Messer. Griesheim GmbH, Fed. Rep. of Germany

[21] Appl. No.: 906,072

[22] Filed: Sep. 11, 1986

[30] Foreign Application Priority Data

Sep. 28, 1985 [DE] Fed. Rep. of Germany ....... 3534629

[51] Int. Cl.[4] ............................................. A61H 33/06
[52] U.S. Cl. ..................................... 128/374; 128/367; 128/373; 128/DIG. 27
[58] Field of Search ............... 128/374, 371, 375, 373, 128/367, 368, DIG. 27, 395, 396, 400

[56] References Cited

U.S. PATENT DOCUMENTS

| | | | |
|---|---|---|---|
| 185,622 | 12/1876 | Brown | 128/374 |
| 222,690 | 12/1879 | Goldschmidt | 128/375 |
| 318,760 | 5/1885 | Lester | 128/373 |
| 363,423 | 5/1887 | Schoenecker | 128/374 |
| 478,385 | 7/1892 | Whiteley | 128/374 |
| 1,028,326 | 6/1912 | Burdick | 128/374 |
| 1,694,858 | 12/1928 | Landon | 128/374 |
| 2,240,819 | 5/1941 | Waly | 128/373 |
| 2,640,201 | 6/1953 | Burwell | 128/373 |
| 2,702,552 | 2/1955 | Moodie | 128/375 |
| 3,161,192 | 12/1964 | McCormack | 128/DIG. 27 |
| 3,902,488 | 9/1975 | Sheppard | 128/367 |
| 4,105,036 | 8/1978 | McGrath | 128/374 |
| 4,335,724 | 6/1982 | Frei et al. | 128/373 |

FOREIGN PATENT DOCUMENTS

| | | | |
|---|---|---|---|
| 712650 | 10/1941 | Fed. Rep. of Germany | 128/371 |
| 953108 | 11/1949 | France | 128/373 |

Primary Examiner—Michael Safavi
Attorney, Agent, or Firm—Connolly & Hutz

[57] ABSTRACT

A device for carrying out cryotherapy on the entire body with a cold treatment gas includes a cabin formed by shells which face one another an enclose the patient and which have opposing openings for the entry and exit of the treatment gas and which further allow the patient's head to remain free.

11 Claims, 2 Drawing Sheets

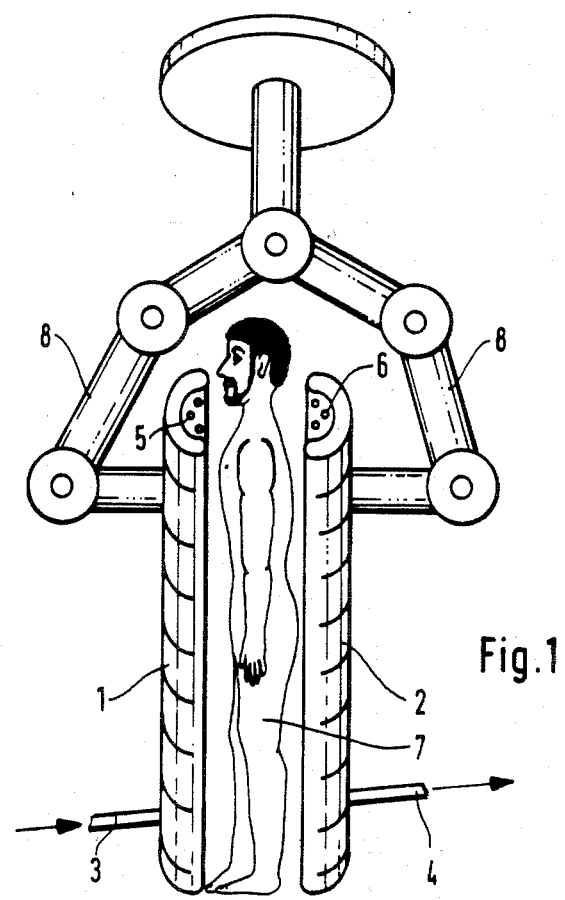
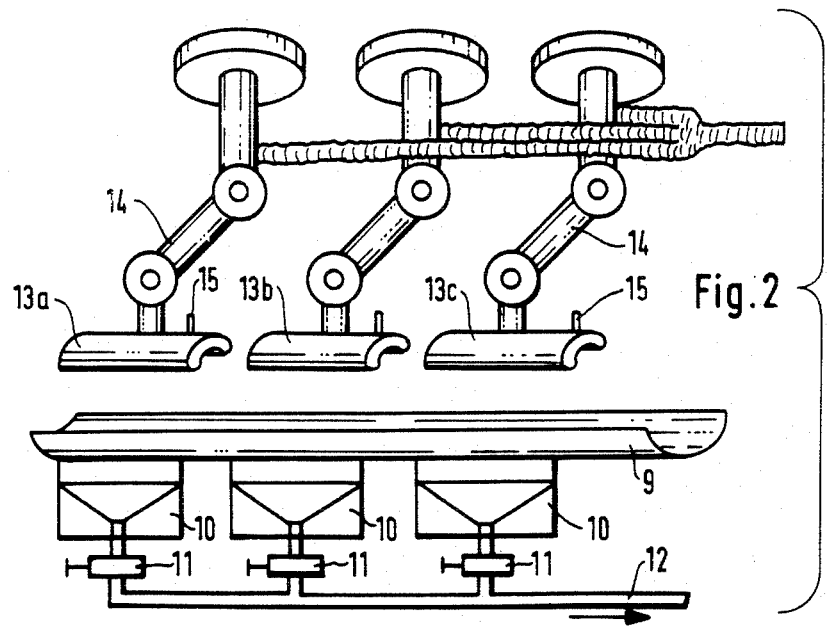

DEVICE FOR CARRYING OUT CRYOTHERAPY

BACKGROUND OF INVENTION

The invention is concerned with a device for carrying out cryotherapy on the entire body with a cold treatment gas according to the concept of claim 1.

Aside from the local cryotherapy carried out since a few years ago with a cold treatment gas, e.g. for treatment of rheumatic diseases, a cryotherapy on the entire body is also carried out with some forms of illnesses. Air is hereby cooled in heat exchangers, with the aid of liquid nitrogen, and injected into closed chamber. This chamber or device has walls of insulating material and connections for the supply and removal of the treatment gas. Such a chamber is, for example, disclosed in the Japanese utility patent No. 168 125/81. is concept finds little approval, however, from doctors as well as from patients. the reasons for this are manyfold. The patients object to the lack of direct contact with the doctor since during, treatment, only an indirect contact through speaker arrangements is possible. The strong buildup of fog in the chamber further intensifies this impression of lack of direct contact. Another disadvantage is the undesirable cooling in the area of the head of the patient and around him Aside from this one must, by special means, avoid the inhalation of cold air. Regardless of this, such chambers require a high investment cost. Because of the long buildup time, there is a need for continuous operation, as a result of which relatively high operation costs result. The supervision of the patient during treatment is expensive.

SUMMARY OF INVENTION

The objective of the invention is to provide a device for carrying out cryotherapy on the entire body with a cold treatment gas, which permits direct contact between physician and patient during treatment, which leaves the head of the patient free and which, because of shorter buildup times, does not require continuous operation.

The cryotherapy cabin of this invention is formed by opposing shells having entrance and exit openings for the treatment gas.

THE DRAWINGS

FIG. 1 is a device for treating a standing patient;

FIG. 2 is a device for treating a patient who is lying down; and

DETAILED DESCRIPTION

Figure 3:
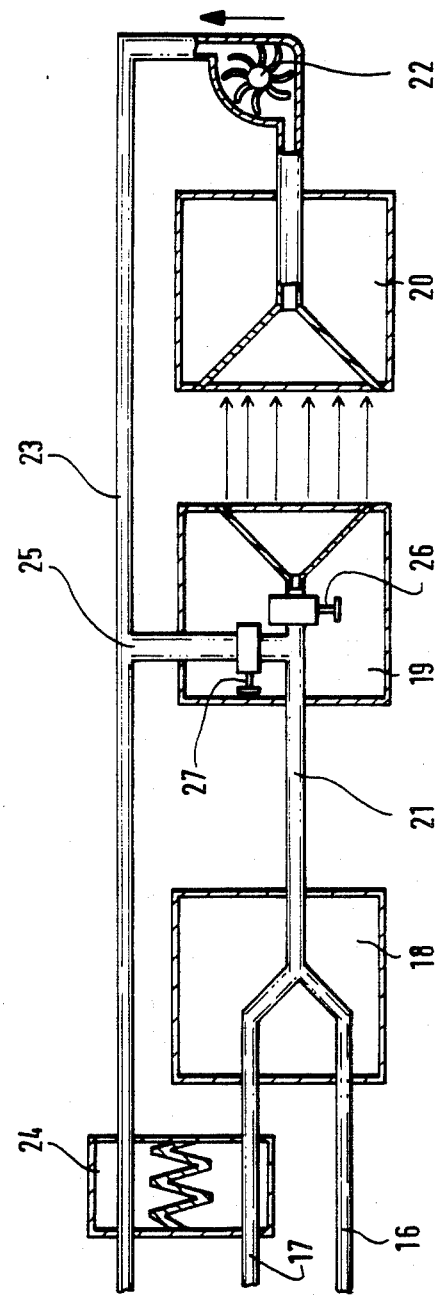
FIG. 3 is an apparatus for producing the treatment gas, which allows economical idling operation of the device.

The device illustrated in FIG. 1 consists of two cylindrical half shells 1, 2 which enclose its treatment chamber. The cold treatment gas enters the shell 1 and is drawn out of shell 2 via the line 4. The shells 1, 2 are of such a height that the head of the patient 7 remains outside of the treatment chamber. On its inner side of its shells 1, 2, are the openings 5, 6 by means of which the treatment gas flows in or out of the treatment chamber. A vertical gas flow then occurs on the body of the patient 7 and around him.

The distance of the shells 1, 2 from one another can be fixed in the simplest manner by means of manually operated bolts which connect its shells 1, 2 to one another. The jointed arms 8, which are attached to its shells 1, 2 and mounted on the ceiling of the clinic room allow for a particularly good space utilization. By means of the jointed arms 8, the position of the shells 1, 2 can be adapted to each individual treatment situation.

The openings 5 are purposely arranged and dimensioned in the form of a matrix on the inner side of the shell 1 so that a gas flow from its entire concave surface of the shell 1 occurs when a cold treatment gas is fed via the line 3. The removal of the treatment gas, via the openings 6 on the inner side of the shell 2 and via the line 4, directing the gas to flow directly across from shell 1 to shell 2. The directed gas flow ensures that the entire body, with the exception of the head region, is cooled.

While FIG. 1 shows an embodiment of the invention for treating a standing patient, FIG. 2 shows an embodiment of the invention for treating a patient which is lying down. The fundamental principle of the treatment chamber formed by cylindrical shells which leave the face of the patient fee is maintained here. The shell 9 which serves to draw off the treatment gas is, in this case, designed as a grate. The patient is bedded down on this. Underneath the shell 9, there are suction funnels 10, which are connected to the outlet line 12 by means of the sealing valves 11.

The shell for supplying the treatment gas is subdivided and consists of the three partial shells 13a, 13b, 13c. The gas outlet openings 13a, 13b, 13c in these partial shells are designated like those in FIG. 1. Each partial shell can be lifted up toward the ceiling of the clinic room by means of a jointed arm 14. The supply of the cold treatment gas occurs by means of hoses which are connected to the connections 15.

All common equipment and gas compositions can be used to produce the cold treatment gas. The treatment gas is preferably produced from a liquefiable gas, especially nitrogen, and dry air. As a result, the invention can be practiced, in a simple manner, an including having economical idle operation. A device suited for this purpose is shown in FIG. 3. Liquid nitrogen is introduced via the line 16 and dry air is introduced via line 17 into the mixing device 18. The treatment gas formed in the mixing device 18 flows through the line 21 into the intake shell 19. The intake shell 19 corresponds to shell 1 in FIG. 1 and to shells 13a, 13b, 13c in FIG. 2. The cold treatment gas flows through the treatment chamber between the shells, with the patient in it, and reaches the outlet shell 20 which corresponds to the shells 2 and 9 respectively in FIGS. 1 and 2. From the outlet shell 20, it is drawn through the suction blower 22 and channeled through the heat exchanger 24 by means of the line 23. In the heat exchanger 24, it transfers its cold to its entering air in its line 17. In this manner, the cooling is optimally utilized during the operation of the device according to its invention. The suctioning causes a directed flow and serves to reclaim the cooling and stabilizes the oxygen concentration in the clinic room.

When no patient is being treated, but the device needs to be kept ready, the device is switched to idling mode. During idling, the cold treatment gas flows directly back to the heat exchanger 24 via the line 25. Switching to idling mode is accomplished by actuating the valves 26 and 27. The idle operation is purposely maintained with a smaller amount of gas. It only needs to ensure that the cold wind producing installation be kept cold and supply of gas be maintained. The device according to the invention is thus ready, even during pauses in treatment, and can be heated on a short term basis. An additional advantage consists of the fact that the patient does not have to be positioned under cold conditions. Not shown in FIGS. 1 and 2 are the customary control and safety devices, especially an oxygen sensor in the heat region of the patient which automatically stops the cooling operation in the event of a shortage of oxygen in the breathing air, for example as a result of a malfunction. The infrared probes in the shells 1 and 13a, 13b, 13c serve to continually monitor the skin temperature of the patient. The embodiment illustrated in FIG. 2 also permits the partial treatment of major areas of the patient's body. In such an event, only the appropriate partial shell is impacted with the cold treatment gas. In contrast to the prior cold chambers, the buildup period with the device according to the invention is extremely short, there is, therefore, no need for an expensive continuous operation. A direct voice contact between the patient and the physician is possible at any time during the treatment. The head of the patient is kept free of the cold treatment gas, and therefore the expensive prior safety measures can be waived.

SUMMARY

Cryotherapy on the entire body with cold treatment gas in closed devices has severaldisadvantages. These consist, on the one hand, of psychological barriers on the patient's part since, in spite of various communication media, direct contact between the physician and the patient is not possible. On the other hand, the unwanted cooling of the patient's head occurs and precautions must be taken to prevent the patient from inhaling the cold treatment gas. In order to avoid this deficiency, the cabin is formed by opposing shells 1, 2 which contain the patient and which leave its face of the patient free. The shells have, on their opposing inner sides, openings 5, 6 respectively for the intake and suctioning off the treatment gas. The shells can be arranged vertically for containing standing patients and horizontally for containing patients which are lying down.

What is claimed is:

1. In a device for carrying out cryotherapy on a body of a patient with a cold treatment gas, consisting of a cabin which is at least mostly enclosed, for containing the patient and which has connections for supplying and removing the treatment gas, the improvement being in that said cabin is formed by curved shells which curve toward one another and are spaced apart and out of contact with one another to enclose the patient permitting the patient's head to remain free of the treatment gas, and said shells having opposing openings for the entry and exit of the treatment gas.

2. Device according to claim 1, characterized by two vertically arranged shells for containing a standing patient.

3. Device according to claim 1 characterized by said shells being horizontally arranged upper and lower shells for containing a patient who is lying down, whereby said lower shell serves to draw off the treatment gas in said lower shell.

4. Device according to claim 3 characterized therein that said upper shell is designed to be of several parts.

5. In a clinic room for carrying out cryotherapy on a body of a patient with a cold treatment gas, consisting of a cabin which is at least mostly enclosed, for containing the patient and which has connections for supplying and removing the treatment gas, the clinic room having a ceiling, the improvement being in that said cabin is formed by two vertically arranged curved shells which curve toward one another and are spaced apart and out of contact with one another to enclose a standing patient permitting the patients' head to remain free of the treatment gas, said shells having opposing openings for the entry and exit of the treatment gas, jointed arms mounted onto said ceiling of said clinic room and to said shells, and said jointed arms being movable from a resting position to permit a movement of said shells to various operating positions.

6. In a clinic room for carrying out cryotherapy on a body of a patient with a cold treatment gas, consisting of a cabin which is at least mostly enclosed, for containing the patient and which has connections for supplying and removing the treatment gas, the clinic room having a ceiling, the improvement being in that said cabin is formed by curved shells which curve toward one another and are spaced apart and out of contact with one another to enclose the patient permitting the patient's head to remain free of the treatment gas, said shells having opposing openings for the entry and exit of the treatment gas, said shells comprising horizontally arranged upper and lower shells for containing a patient who is lying down, whereby said lower shell serves to draw off the treatment gas, said upper shell being formed of several parts, and jointed arms being attached to said ceiling of said clinic room and to said upper shell to permit the movement of said upper shell from a nonoperative position to an operative position when the patient is enclosed between said shells.

7. In a process for cryotherapy on a body of a patient by using a cabin having opposed treatment gas inlet and outlet openings and wherein a treatment gas is formed by mixing dry air with a cold liquified gas which vaporizes to form the treatment gas, the improvement being in that the cabin is formed by providing curved shells which are spaced apart and which curve toward each other, placing the patient between the shells with the head of the patient extending beyond the shells, directing the treatment gas out of gas inlet openings in one of the shells and into outlet openings in an opposing shell without directing the treatment gas toward the head of the patient.

8. In the method of claim 7 wherein the shells are vertically arranged, and the patient is standing between the shells.

9. In the method of claim 7 wherein the shells are horizontally arranged to provide an upper shell and a lower shell, and the patient is lying on the lower shell.

10. In the method of claim 9 including forming the upper shell by a plurality of spaced shell parts.

11. In the method of claim 7 wherein the patient is out of contact with at least one of the shells

* * * * *